United States Patent
Otani et al.

(10) Patent No.: US 6,348,872 B1
(45) Date of Patent: Feb. 19, 2002

(54) GAS DETECTOR-ALARM EMPLOYING HOT-WIRE GAS SENSOR

(75) Inventors: Seiichi Otani; Shoei Yasuda, both of Tokyo (JP)

(73) Assignee: Riken Keiko Co., Ltd., Tokyo (JP)

(*) Notice: Subject to any disclaimer, the term of this patent is extended or adjusted under 35 U.S.C. 154(b) by 0 days.

(21) Appl. No.: 09/693,917

(22) Filed: Oct. 23, 2000

(30) Foreign Application Priority Data

Sep. 14, 2000 (JP) .......................................... 2000-280009

(51) Int. Cl.[7] .............................................. G08B 17/10
(52) U.S. Cl. ........................ 340/632; 340/633; 340/634; 340/693.3
(58) Field of Search .................................. 340/632, 633, 340/634, 693.3, 516, 526, 520

(56) References Cited

U.S. PATENT DOCUMENTS

| | | | | |
|---|---|---|---|---|
| 4,340,885 A | * | 7/1982 | Chavis et al. ................ | 340/632 |
| 4,740,387 A | * | 4/1988 | Manaka ....................... | 427/125 |
| 4,966,033 A | * | 10/1990 | Nishimura et al. .......... | 73/118.2 |
| 5,608,384 A | * | 3/1997 | Tikijian ....................... | 340/632 |

* cited by examiner

*Primary Examiner*—Jeffery Hofsass
*Assistant Examiner*—Daniel Previl
(74) *Attorney, Agent, or Firm*—Connolly Bove Lodge & Hutz

(57) ABSTRACT

A gas detector-alarm comprises a hot-wire gas sensor 1 having an actuating power control 7 that supplies pulsed actuating power with a cycle T0 when the concentration of gas detected by the hot-wire gas sensor is lower than a first reference level, with a cycle T1 that is shorter than said cycle T0 at least once when the concentration of gas exceeds a second reference level, and with a cycle T0 again after an alarm has been triggered.

1 Claim, 2 Drawing Sheets

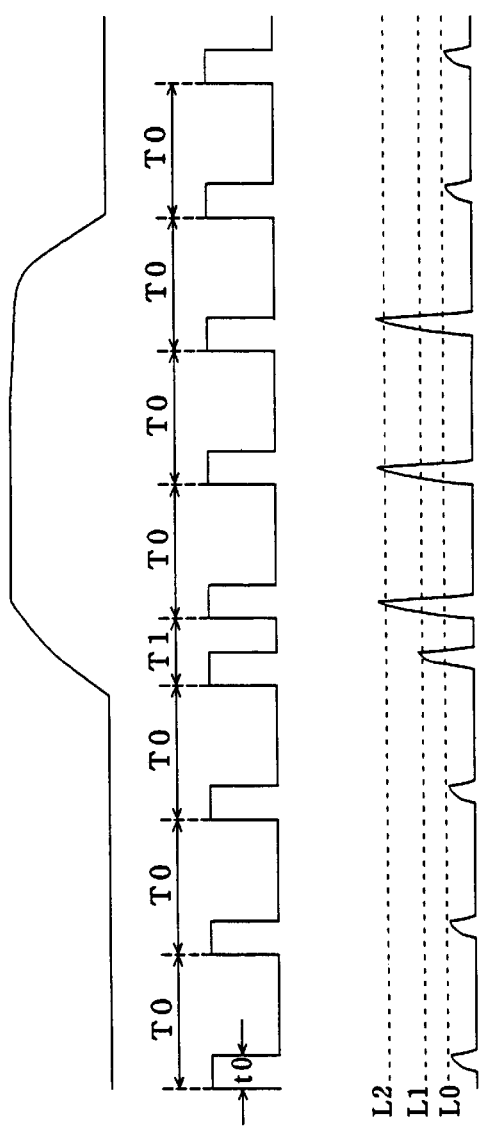
FIG. 2(a) gas concentration
FIG. 2(b) actuating power
FIG. 2(c) detection signal

GAS DETECTOR-ALARM EMPLOYING HOT-WIRE GAS SENSOR

FIELD OF THE INVENTION

This invention relates to a gas detector-alarm employing a hot-wire gas sensor and more particularly to a technology to reduce electric power to heat the heat wire.

DESCRIPTION OF THE PRIOR ART

With gas detectors that determine gas concentration by means of a gas sensor with a hot wire, most of electric power supplied thereto is consumed by the gas sensor. As such, provisions are made to supply electricity to the hot wire at given intervals for the shortest possible but long enough time to permit gas detection, as proposed in Japanese Provisional Utility Model Publication No. 14595 of 1987, and, in addition to the above, to ensure continued supply of electricity when the presence of gas is detected, as proposed in Japanese Provisional Patent Publication No. 233699 of 1991.

To detect transient changes in gas concentration after the occurrence of gas leakage by these methods, however, heating time must be increased, with a resulting increase in power consumption during the time when gas is present.

The latter of the above two methods, although capable of detecting transient changes in gas concentration, involves the problem that power consumption increases when the concentration of gas present exceeds a certain level.

SUMMARY OF THE INVENTION

A gas detector-alarm according to this invention determines gas concentration by means of a hot-wire gas sensor to which pulsed actuating current is supplied. Said gas detector-alarm has an actuating-current control unit that supplies said pulsed actuating current with a cycle T0 when the concentration of gas detected by said hot-wire gas sensor is lower than a first reference level and with a cycle T1, which is shorter than said cycle T0, at least once when the concentration is higher than a second reference level.

When gas concentration exceeds the first reference level, the current-supply cycle is reduced to T0 in preparation for further concentration increase. When gas concentration is found to exceed the second reference level and reaches the warning level, the current-supply cycle is increased to T1 to save electricity in the presence of high-concentration gas.

The object of this invention is to provide a gas detector-alarm employing a hot-wire gas sensor that triggers an alarm without failure within a predetermined time while keeping to a minimum power consumption after gas concentration has exceeded a given level.

BRIEF DESCRIPTION OF THE DRAWINGS

FIG. 2 is a waveform showing the operation of the same embodiment.

DESCRIPTION OF THE PREFERRED EMBODIMENT

Figure 1:
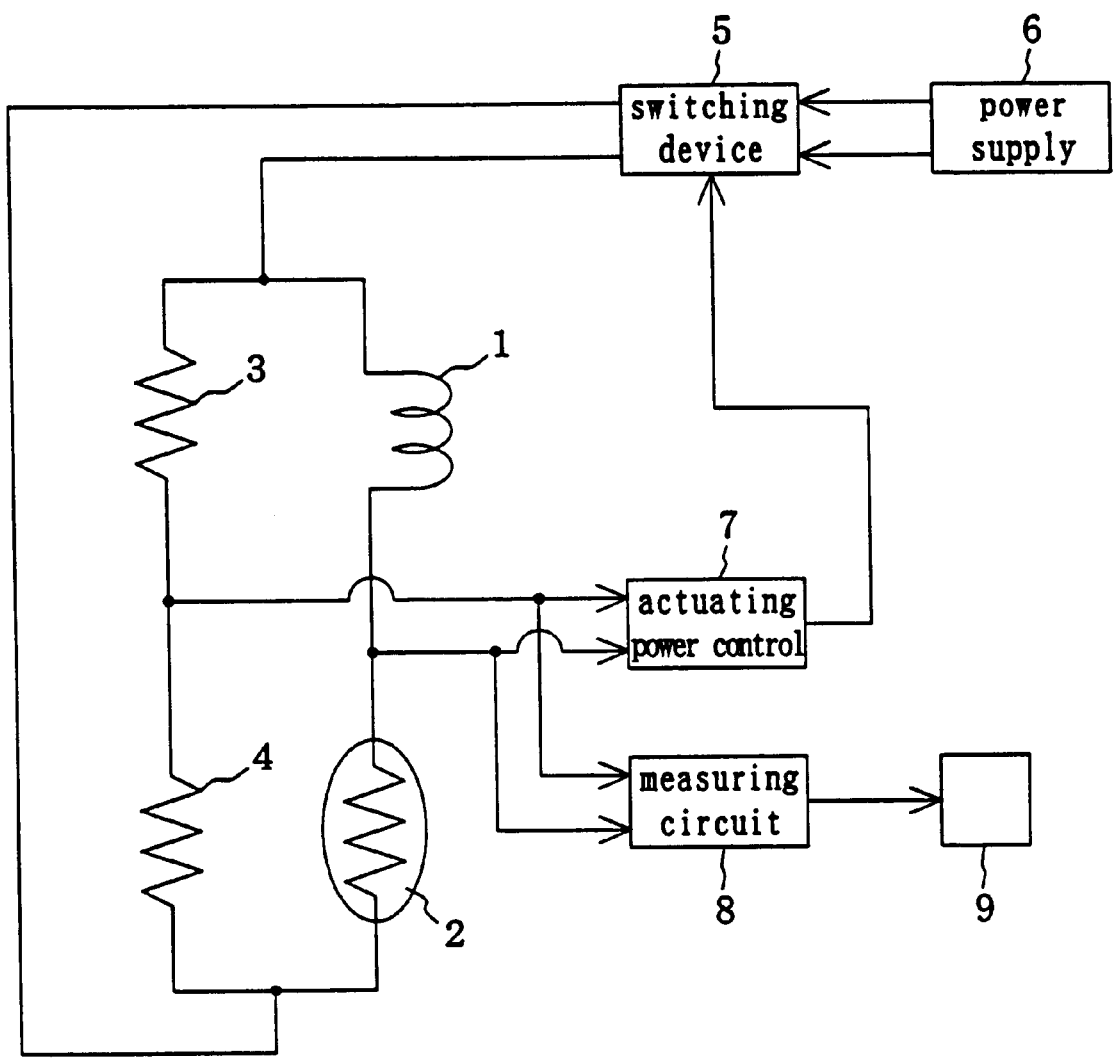
FIG. 1 is a block diagram of an embodiment of a gas detector-alarm according to this invention.

FIG. 1 shows an embodiment of a gas detector-alarm according to this invention. A hot-wire gas sensor 1 alters electric resistance by detecting the difference in thermal conductivity of gases and comprises a bridge formed of a temperature-compensated resistor 2 and fixed resistors 3 and 4. The actuating power terminal of the hot-wire gas sensor is connected to a power supply 6 via a switching device 5, whereas the detecting terminal thereof is connected to an actuating power control 7 that controls the operation of the switching device 5.

The actuating power control 7 supplies a pulsed actuating power with a time width t0 as shown in FIGS. 2(a) to 2(c). The actuating power control 7 is adapted to supply the actuating power with a cycle T0 when the hot-wire gas sensor 1 does not detects any gas or the bridge outputs a detection signal representing a detection output lower than the noise level L0 and with a cycle T1, which is shorter than the cycle T0, when the bridge outputs a detection signal representing a gas concentration higher than a predetermined concentration or above a warning level L1. Reference numeral 8 designates a measuring circuit that actuates an alarm indicator 9 based on the detection signal from the bridge.

The time width t0 of the actuating power is set at a length of time in which the hot-wire gas sensor 1 is heated from ordinary temperature to a temperature at which normal gas detection can be made. In the case of this embodiment, the temperature permitting normal gas detection and time width t0 are several hundreds degrees centigrade and approximately 2 seconds, respectively.

The cycle T1 is not shorter than an interval of time between the start of measurement by the hot-wire gas sensor a and a time point at which a gas admitted into a cell in the hot-wire gas sensor 1 is replaced that is long enough to permit an alarm to be triggered within a given time after the concentration of the gas ahs exceeded a predetermined level. The cycle T1 in this embodiment is set at 4 seconds.

In the absence of gas, the actuating power control 7 of this embodiment supplies the pulsed actuating power to the bridge that constitutes the gas sensor 1 with a cycle T0. Accordingly, the gas sensor 1 becomes quiescent after it has been heated to a high enough temperature to permit gas detection, thus eliminating the waste of power by the gas sensor 1.

When gas leakage occurs and the detection signal exceeds level L1, the actuating power control 7 shortens the power supply cycle from T0 to T1. Even if, as such, gas concentration increases suddenly to above the warning level, a detection signal representing a concentration above warning level L3 is triggered whereby the measuring circuit 8 promptly actuates the alarm indicator 9 to trigger an alarm. After the alarm has been provided, the actuating power control 7 lengthens the power supply cycle to T0 and thereby eliminates the waste of power. The hot wire is coated with a catalytic substance that reacts with the gas detected to prevent overheating by high-concentration gases and possible shortening of the service life of the gas sensor.

While the embodiment described above detects resistance caused by the temperature changes of the hot wire due to the difference in thermal conductivity of gases, a hot wire coated with a catalytic or other active substance also performs the same function by detecting the heat of reaction as resistance.

What is claimed is:

1. In a gas detector-alarm employing a hot-wire gas sensor detecting gas concentration by means of a pulsed actuating power supplied thereto, the improvement which comprises a hot-wire gas sensor having an actuating power control that supplies said pulsed actuating power with a cycle T0 when the concentration of gas detected by said hot-wire gas sensor is lower than a first reference level, with a cycle T1 that is shorter than said cycle T0 at least once when the concentration of gas exceeds a second reference level, and with a cycle T0 after an alarm has been triggered.

* * * * *